US00PP22752P2

(12) United States Plant Patent
Smith

(10) Patent No.: US PP22,752 P2
(45) Date of Patent: May 22, 2012

(54) ***ASTER* PLANT NAMED 'SYNHEN THEFIRST'**

(50) Latin Name: *Aster hybrida*
Varietal Denomination: Synhen Thefirst

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 23 days.

(21) Appl. No.: 12/925,435

(22) Filed: Oct. 21, 2010

(51) Int. Cl.
*A01H 5/00* (2006.01)

(52) U.S. Cl. ..... Plt./355

(58) Field of Classification Search ..... Plt./355
See application file for complete search history.

*Primary Examiner* — June Hwu
(74) *Attorney, Agent, or Firm* — Joshua L. Price

(57) ABSTRACT

A new *Aster* plant named 'Synhen Thefirst' particularly distinguished by the small to medium sized, long lasting, double-type inflorescences with violet ray floret color, medium green foliage; upright, freely branched and rounded plant habit, and a natural season flowering in early September.

1 Drawing Sheet

Latin name of the genus and species of the plant claimed: *Aster hybrida.*

Varietal denomination: 'Synhen Thefirst'.

BACKGROUND OF THE NEW PLANT

The present invention comprises a new *Aster*, botanically known as *Aster hybrida*, and hereinafter referred to by the variety name 'Synhen Thefirst'.

'Synhen Thefirst' originated from an open-pollinated hybridization made in March 2006 in a controlled breeding environment in Alva, Fla. The female parent was the unpatented, proprietary plant designated 'AS04-036' with lavender ray floret color. 'AS04-036' has a more compact plant habit with more vigor than 'Synhen Thefirst'.

'Synhen Thefirst' originated from an open-pollinated hybridization made in March 2006 in a controlled breeding environment in Alva, Fla. The female parent was the unpatented, proprietary plant designated 'AS04-036' with lavender ray floret color. 'AS04-36' has a more compact plant habit with more vigor than 'Synhen Thefirst'.

The male parent of 'Synhen Thefirst' was an unknown plant. The resultant seed was sown in late May 2006. 'Synhen Thefirst' was selected as one flowering plant within the progeny of the stated cross in late October 2006 in a controlled environment in Alva, Fla.

The first act of asexual reproduction of 'Synhen Thefirst' was accomplished when vegetative cuttings were propagated from the initial selection in December 2006 in a controlled environment in Alva, Fla.

BRIEF SUMMARY OF INVENTION

Horticultural examination of plants grown from cuttings of the plant initiated in December 2006, and continuing thereafter, has demonstrated that the combination of characteristics as herein disclosed for 'Synhen Thefirst' are firmly fixed and are retained through successive generations of asexual reproduction.

'Synhen Thefirst' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6777). 'Synhen Thefirst' has not been made publicly available more than one year prior to the filing of this application.

The following traits have been repeatedly observed and are determined to be basic characteristics of the new variety. The combination of these characteristics distinguishes this *Aster* as a new and distinct variety.

BRIEF DESCRIPTION OF THE PHOTOGRAPHS

The accompanying photographic drawing shows typical flower and foliage characteristics of 'Synhen Thefirst' with colors being as true as possible with an illustration of this type.

The photographic drawing shows three flowering potted plants of the new variety growing within one pot and a close-up of the flowers.

DETAILED BOTANICAL DESCRIPTION

The plant descriptions, measurements and aforementioned photographs were taken in Gilroy, Calif. in May 2010 under natural light. These plants used in the photograph and descriptions were about 12 weeks old. Plants were grown in an 8 inch pot with three plants per pot.

Color references are made to The Royal Horticultural Society Colour Chart (R.H.S.) 2001.

TABLE 1

DIFFERENCES BETWEEN THE NEW VARIETY 'SYNHEN THEFIRST' AND A SIMILAR VARIETY: 'VICTORIA FANNY' (U.S. Plant Pat. No. 13,360)

| | 'Synhen Thefirst' | 'Victoria Fanny' (U.S. Plant Pat. No. 13,360) |
|---|---|---|
| Quantity of disc florets: | More | Less |
| Plant habit: | More compact/rounder | Less compact/more upright |
| Black cloth flowering response: | About 5 days faster | About 5 days slower |

Plant:
*Form, growth and habit*.—Stems upright, freely branching, rounded habit; strong and moderately vigorous growth.
*Plant height*.—About 20 cm.
*Plant height* (*inflorescence included*).—25-28 cm.
*Plant width*.—30-38 cm.
*Garden performance and tolerance to weather*.—Very good.

Roots:
*Number of days to initiate roots*.—10 days at about 22 degrees C.
*Number of days to produce a rooted cutting*.—16-18 days at 22 degrees C.
*Type*.—Fine, fibrous, free branching.
*Color*.—RHS N155B but whiter.

Foliage:
*Arrangement*.—Alternate, simple, sessile.
*Immature, leaf color, upper surface*.—Between RHS 137A and RHS 137B.
*Lower surface*.—RHS 137B.
*Mature, leaf color, upper surface*.—Closest to RHS 137A.
*Lower surface*.—RHS 137B.
*Length*.—4.7-5.1 cm.
*Width*.—1.2-1.45 cm.
*Shape*.—Oblong.
*Base shape*.—Clasping.
*Apex shape*.—Acute.
*Margin*.—Entire.
*Texture, upper surface*.—Mostly glabrous, but pubescent on the margins.
*Lower surface*.—Mostly glabrous, but pubescent on the margins.
*Color of veins, upper surface*.—RHS 144A basally becoming indistinct.
*Color of veins, lower surface*.—RHS 144A basally becoming indistinct.

Stem:
*Quantity of main branches per plant*.—About 5 with an abundance of secondary branching.
*Color of stem*.—RHS 138A.
*Length of stem*.—20.0 cm.
*Diameter*.—0.2-0.25 cm.
*Length of internodes*.—0.5-1.0 cm.
*Texture*.—Slightly hirsute.
*Color of peduncle*.—RHS 138A.
*Length of peduncle*.—1.5-2.5 cm.
*Peduncle diameter*.—0.1-0.15 cm.
*Texture*.—Very slightly hirsute.

Inflorescence:
*Type*.—Compositae type, solitary inflorescences borne terminally above foliage, ray florets arranged acropetally on a capitulum.
*Natural season flowering*.—In earlier September in the north.
*Quantity of inflorescences per plant*.—About 50-60 with numerous buds.
*Lastingness of individual blooms on the plant*.—About 3-4 weeks.
*Fragrance*.—None.

Bud (just when opening/showing color):
*Color*.—RHS 86C.
*Length*.—0.5-1.0 cm.
*Width*.—0.6-0.8 cm.
*Shape*.—Oblate.

Immature inflorescence:
*Diameter*.—2.3-2.5 cm.
*Color of ray florets, upper surface*.—RHS N87A but a little darker, with RHS 85D basally.
*Lower surface*.—RHS N87C.

Mature inflorescence:
*Diameter*.—3.3-3.6 cm.
*Depth*.—1.5 cm.
*Total diameter of 'disc'*.—1.2-1.3 cm.
*Receptacle height*.—0.3 cm.
*Receptacle diameter*.—0.3 cm.

Ray florets:
*Average quantity of florets*.—About 175 in numerous whorls.
*Color of florets, upper surface*.—RHS N87B to RHS N87C with RHS N87A basally.
*Lower surface*.—RHS N88D with RHS 91D basally.
*Length*.—1.5-1.6 cm.
*Width*.—0.25-0.3 cm.
*Shape*.—Oblong.
*Apex shape*.—Rounded, retuse and praemorse.
*Margin*.—Entire.
*Texture, upper surface*.—Papillose.
*Lower surface*.—Papillose.

Disc florets:
*Average quantity of florets*.—About 75.
*Color of florets*.—RHS 3B with a hint of RHS 37D when maturing.
*Length*.—0.4-0.5 cm.
*Width*.—0.15-0.2 cm.
*Shape*.—Tubular, elongated.
*Apex shape*.—Acute, 5 pointed.

Phyllaries:
*Quantity*.—About 35.
*Color, upper surface*.—Closest to RHS 137A.
*Lower surface*.—Closest to RHS 137A.
*Length*.—0.5 cm.
*Width*.—0.1 cm.
*Shape*.—Lanceolate.
*Apex shape*.—Acute.
*Based*.—Fused.
*Margins*.—Entire.
*Texture, upper surface*.—Glabrous.
*Lower surface*.—Glabrous.

Reproductive organs:
*Gynoecium*.—Present on both florets.
*Pistil*.—1.
*Length*.—0.5 cm.
*Style color*.—RHS 155C.
*Style length*.—0.4 cm.
*Stigma color*.—RHS 60C.
*Stigma shape*.—Bi-parted.
*Ovary color*.—Not observed.
*Androecium*.—Present on only disc florets.
*Stamens*.—1.
*Color of filaments*.—About RHS 1B but more green and translucent looking.
*Length filaments*.—0.2 cm.
*Anther color*.—About RHS 4B.
*Anther length*.—0.1 cm.
*Anther shape*.—Oblong.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Aster* plant named 'Synhen Thefirst' substantially as illustrated and described herein.

* * * * *

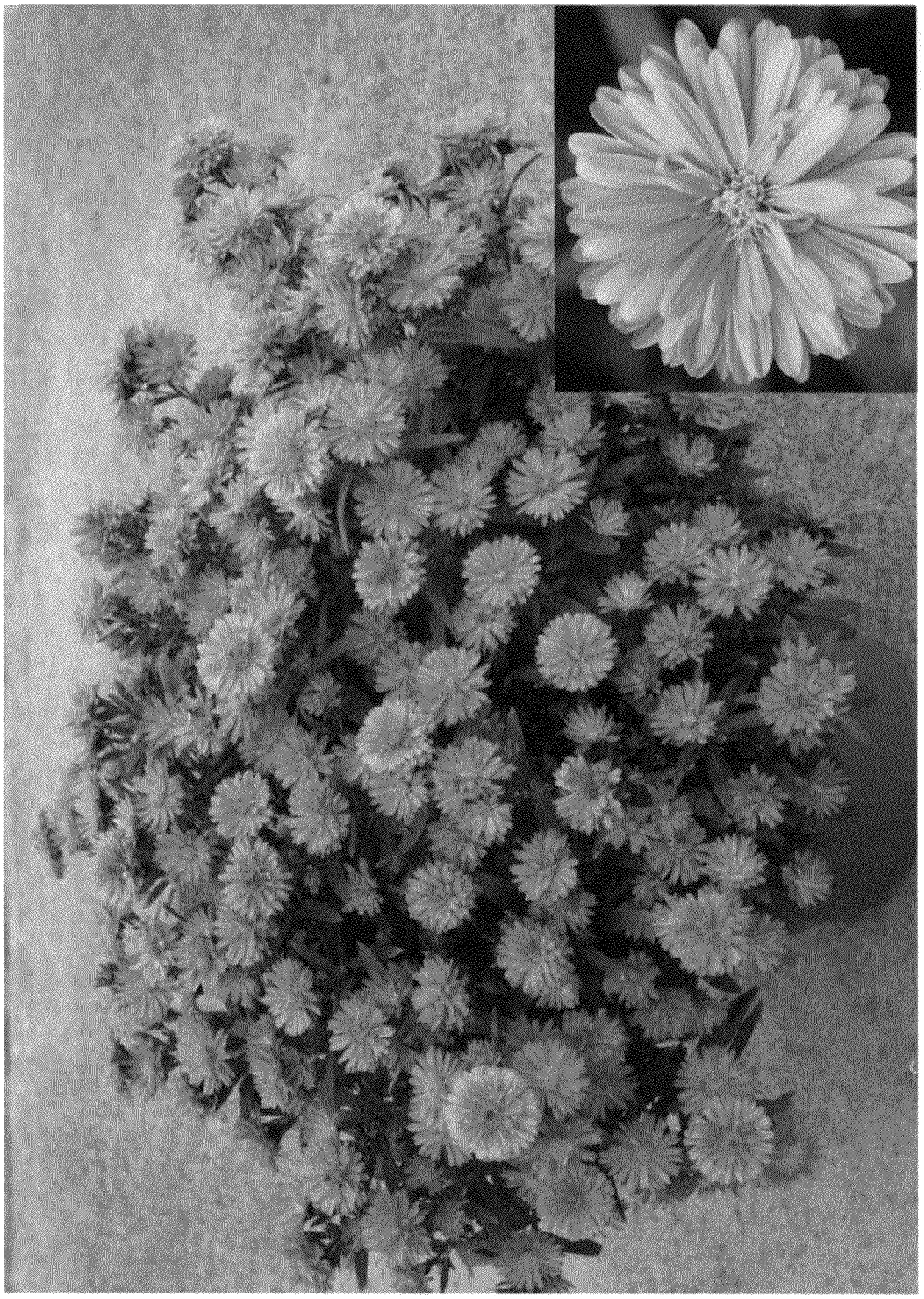

UNITED STATES PATENT AND TRADEMARK OFFICE

CERTIFICATE OF CORRECTION

PATENT NO. : PP22,752 P2
APPLICATION NO. : 12/925435
DATED : May 22, 2012
INVENTOR(S) : Smith It is certified that error appears in the above-identified patent and that said Letters Patent is hereby corrected as shown below:

At column 1, after line 9 and before line 10, please insert the following paragraph:
--'Synhen Thefirst' is a product of a planned breeding program. The new cultivar has small to medium sized, long lasting, double-type inflorescences with violet ray floret color, medium green foliage; upright, freely branched and rounded plant habit, and a natural season flowering in early September.--

At column 1, lines 16-21, please delete the following:
"'Synhen Thefirst' originated from an open-pollinated hybridization made in March 2006 in a controlled breeding environment in Alva, Florida. The female parent was the unpatented, proprietary plant designated 'AS04-036' with lavender ray floret color. 'AS04-36' has a more compact plant habit with more vigor than 'Synhen Thefirst'."

Signed and Sealed this
Third Day of July, 2012

David J. Kappos

David J. Kappos
*Director of the United States Patent and Trademark Office*